United States Patent [19]

Smith et al.

[11] Patent Number: 4,474,786
[45] Date of Patent: Oct. 2, 1984

[54] TRICYCLIC LACTAMS AND DERIVATIVES USEFUL IN INCREASING CARDIAC CONTRACTILITY

[75] Inventors: Elizabeth M. Smith, Verona; Ronald J. Doll, Maplewood; Bernard R. Neustadt, West Orange, all of N.J.

[73] Assignee: Schering Corporation, Kenilworth, N.J.

[21] Appl. No.: 505,050

[22] Filed: Jun. 16, 1983

[51] Int. Cl.$^3$ ............... A61K 31/435; C07D 491/052; C07D 491/044; C07D 513/04
[52] U.S. Cl. .................................... 424/256; 546/80; 546/83; 546/89; 546/92

[58] Field of Search ...................... 546/80, 83, 89, 92; 424/256

[56] References Cited

U.S. PATENT DOCUMENTS 4,117,134  9/1978  Connor et al. ...................... 424/256

Primary Examiner—Alan L. Rotman
Assistant Examiner—Dale A. Bjorkman
Attorney, Agent, or Firm—Anita W. Magatti; Gerald S. Rosen

[57] ABSTRACT

Disclosed are tricyclic lactams and derivatives which are effective in increasing cardiac contractility in humans. These compounds are useful in the treatment of congestive heart failure.

12 Claims, No Drawings

TRICYCLIC LACTAMS AND DERIVATIVES USEFUL IN INCREASING CARDIAC CONTRACTILITY

SUMMARY OF THE INVENTION

This invention relates to certain tricyclic lactams which are useful in increasing cardiac contractility, to pharmaceutical compositions containing such compounds and to a method of treating a human patient by administering an effective amount of such compounds to increase cardiac contractility in said patient.

The compounds of the present invention are represented by the formula

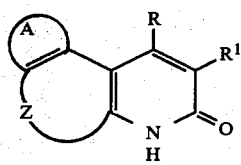

I wherein
R is hydrogen or lower alkyl;
$R^1$ is hydrogen, hydroxy, lower alkoxy, cyano, lower alkyl, halogen, $-NR^2R^3$, $-CONR^2R^3$, $-NHCOR^2$, $-COOR^2$ (wherein $R^2$ and $R^3$ are independently hydrogen, lower alkyl or hydroxy lower alkyl) or

wherein M is sulfur or NH; with the proviso that R and $R^1$ are not both hydrogen;
Z is selected from the group consisting of

 and

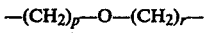

wherein n is 0, 1 or 2; and p and r are independently 0, 1, 2 or 3 with the further proviso that r+p is zero to three;
A is a substituted or unsubstituted benzo or pyrido ring which when substituted has 1 to 3 substituents on the aromatic carbon atoms independently selected from halogen, hydroxy, lower alkyl and lower alkoxy; and pharmaceutically acceptable salts thereof.

Unless otherwise stated, the term "lower alkyl" includes branched- and straight-chain alkyl groups of from 1 to 6 carbon and includes, for example, methyl, ethyl, n-propyl, isopropyl, t-butyl, n-hexyl and the like.

The term "lower alkoxy" includes both branched and straight-chain alkoxy groups of 1 to 6 carbons and includes for example, methoxy, ethoxy, isopropoxy, t-butoxy, n-hexoxy and the like.

The term "halo" or "halogen" means chloro and bromo.

The term "pharmaceutically acceptable salts" includes the pharmaceutically acceptable acid addition salts of the compounds of formula I derived from a variety of organic and inorganic acids, such as sulfuric, phosphoric, hydrochloric, hydrobromic, sulfamic, citric, lactic, oleic, succinic, tartaric, cinnamic, acetic, benzoic, ascorbic and other organic and inorganic acids which form pharmaceutically acceptable addition salts.

The nomenclature employed throughout this specification has been assigned from Parent Compound Handbook (American Chemical Society).

The term A as a "pyrido ring" means the following rings:

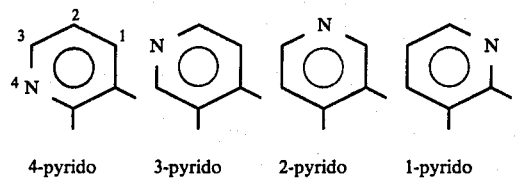

4-pyrido    3-pyrido    2-pyrido    1-pyrido each unsubstituted or substituted with the substituents on the aromatic carbon atoms as described above and with conventional numbering employed therewith.

The 2-oxo-pyridine derivatives (2(1H)-pyridone derivatives) are tautomeric with 2-hydroxy-pyridine derivatives as shown in the partial formulas below:

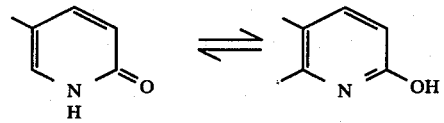

Throughout this specification, the "pyridone" term (e.g. pyridin-3-one) shall be used to mean any of the tautomers.

Preferred R lower alkyl groups are methyl, ethyl, n-propyl and isopropyl. Most preferably R is hydrogen or methyl.

Preferred $R^1$ groups are hydroxy, lower alkoxy, cyano, $-NR^2R^3$, $-CONR^2R^3$, $-NHCOR^2$, wherein $R^2$ and $R^3$ are independently hydrogen, lower alkyl or hydroxy lower alkyl.

More preferred $R^1$ groups are cyano, amino and

Preferably A is a substituted or unsubstituted benzo ring or a 3-pyrido ring.

Preferred lower alkyl substituents on the pyrido and benzo rings are methyl, ethyl, isopropyl, and n-propyl.

Preferred pyrido and benzo lower alkoxy substituents are methoxy, ethoxy, isopropoxy, and n-propoxy.

Particularly preferred are pyrido and benzo substituted with 1 to 3 substituents independently selected from chloro, bromo, amino, methoxy, methyl and hydroxy.

Of the above preferred compounds, those wherein Z is $-OCH_2-$, $-SCH_2$ and $-SO_2CH_2-$ are particularly preferred.

DETAILED DESCRIPTION OF THE INVENTION

The compounds of this invention are useful in increasing cardiac contractility in humans, particularly those suffering congestive heart failure.

The present invention contemplates a method for increasing cardiac contractility in a patient requiring such treatment which comprises administering parenterally a compound of Formula I in an amount effective to increase cardiac contractility.

The compounds are administered in a variety of formulations. Preferably the compounds are administered parenterally. The compounds may be combined with any suitable pharmaceutical carrier and administered in a variety of formulations. The compounds may also be administered transdermally.

Typically, a daily dosage regimen would generally be 0.1 to 10 gm/day parenterally. Preferably, the compounds of this invention should be administered as a constant infusion titrated to the desired clinical effect. The actual dose to be administered is determined by the clinician and is dependent upon various factors such as the particular compound employed and its potency, age and weight of the patient, the severity of the disease, and the individual patient's response. The daily dosage may be administered either singly or divided proportionally into several dosages.

The methods of this invention are implemented using pharmaceutical compositions comprising a pharmaceutically acceptable carrier and an amount of a compound of Formula I effective in increasing cardiac contractility.

In treating certain patients with the compounds of this invention, it is possible to include other compatible pharmaceutically active ingredients in the same dosage unit.

The compounds of this invention may be readily prepared in a two-step synthesis as shown in reactions (1) and (2) below:

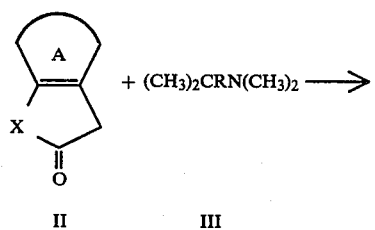

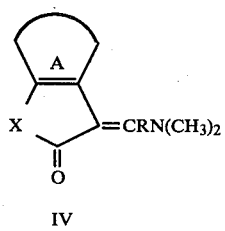

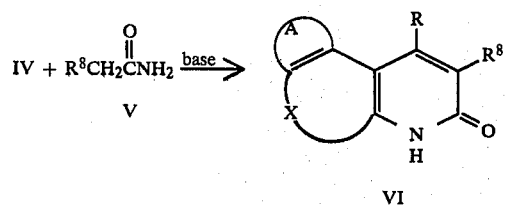

wherein R and A are as defined above, X is $-(CH_2)_p-O-(CH_2)_r-$ or $-(CH_2)_pS(CH_2)_r-$ wherein p and r are as defined above, and $R^8$ is cyano, lower alkoxy or lower alkyl.

Reaction (1) is the condensation of an amide acetal with the active ketone, II, to give IV. For example, the reaction can be conducted by adding an essentially equimolar amount of N,N-dimethylformamide dimethyl acetal, to II. The reaction is generally conducted neat (i.e., without solvent). Reaction pressure is not critical and for convenience the reaction is generally conducted at atmospheric pressure. The reaction is generaly conducted at reflux and is generally complete from within ½ to 4 hours. The product, IV, may then be isolated and purified by conventional procedures such as extraction, filtration, chromatography, distillation, or alternatively, may be used in succeeding reactions without purification.

The cyclization of reaction (2) may be accomplished by addition of 1 to 1.5 equivalents of the substituted acetamide, V, to IV. The reaction is conducted in the liqud phase employing an inert organic solvent such as dimethylformamide. An excess (3 equivalents) of a base such as sodium methoxide, sodium ethoxide and the like is employed in the system. Reaction pressure is not critical and for convenience the reaction is generally conducted at atmospheric pressure. The reaction is generally conducted at from 60° C. to 100° C. and is generally complete from within 2 to 10 hours. The product, VI, may then be isolated and purified by conventional procedures such as extraction, filtration, chromatography, distillation, or alternatively, may be used in succeeding reactions without isolation and/or purification.

Compounds of formula I wherein Z is sulfinyl or sulfonyl may be preferably prepared by oxidation of the corresponding thio compounds.

The 2-cyanopyridin-3-(4H)-ones, VI, are readily derivatized by procedures recognized in the art as shown in the following flow diagram, wherein $X'_2$ is either $Cl_2$ or $Br_2$.

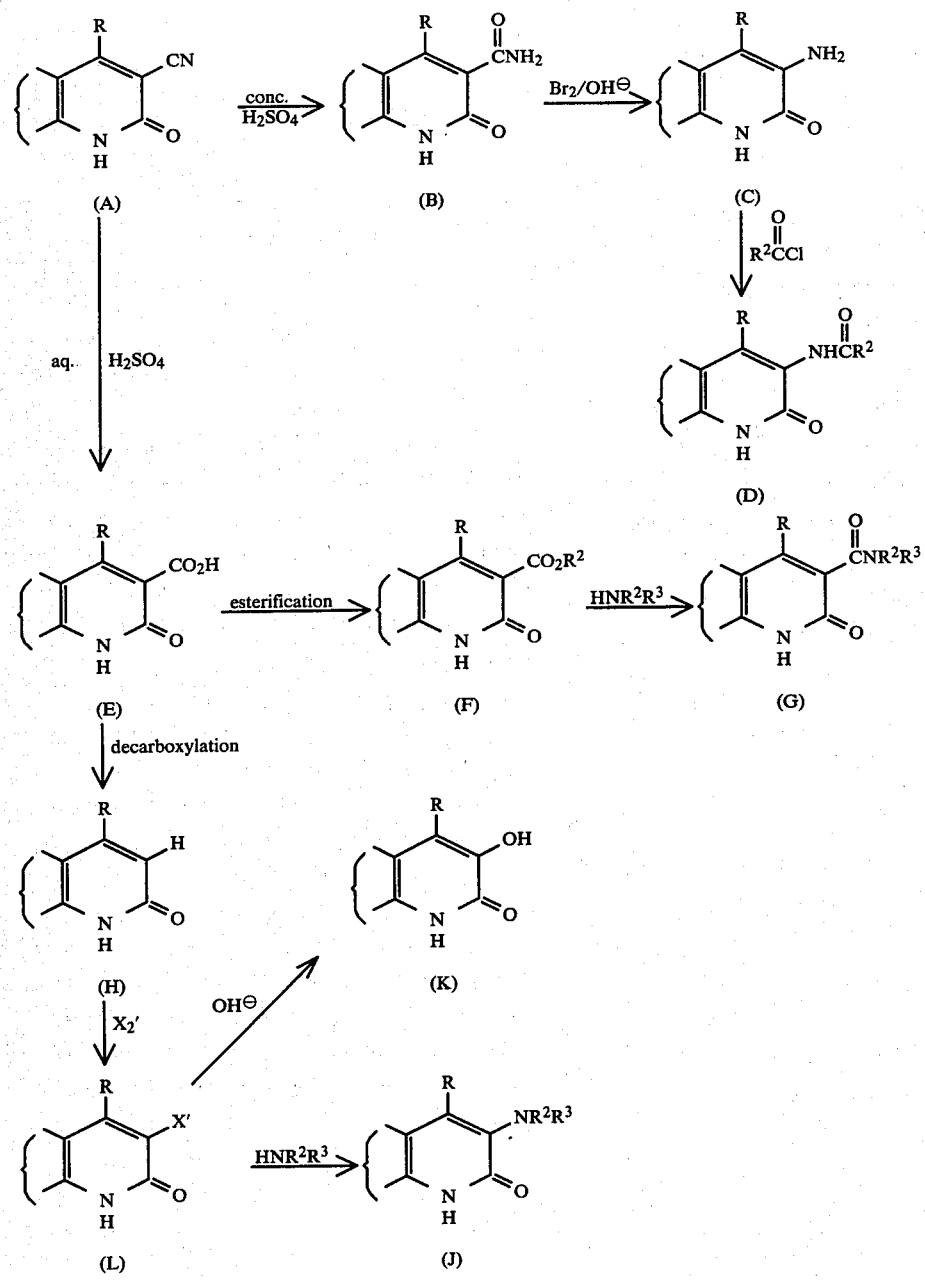

3-cyanopyridin-2(1H)-one(s), (A), are readily converted to the carboxamides, (B), by treatment with concentrated acid such as concentrated sulfuric acid. The carboxamides may then be converted to the amines, (C), by treatment with bromine and a base. The amines may then be acylated by reaction with an acid halide to form (D).

3-cyanopyridin-2(1H)-ones (A) may also be hydrolyzed to the 3-carboxylic acids, (E), by treatment with an aqueous acid such as aqueous sulfuric acid. The carboxylic acids may then be readily esterified under acidic or basic conditions to form the esters, (F).

The esters may be converted to the amides, (G), by treatment with an excess of ammonia or the appropriate amine in either an inert hydroxylic solvent e.g., methanol or ethanol, water, or a mixture of water and an inert hydroxylic solvent.

The 3-carboxylic acids (E) may be readily decarboxylated by heating to produce (H) which may then be treated with chlorine or bromine to produce the 3-halopyridin2(1H)-ones, (L).

The 3-halopyridin-2(1H)-ones, (L), may be treated with ammonia or a mono or diloweralkylamine to produce the 3-amino or 3-mono or diloweralkylamino product (J).

The conversion of the 3-halogen to the 3-hydroxypyridin-3(4H)-one, (K), is described in U.S. Pat. No. 4,225,601, which is incorporated herein by reference. In this conversion, a mixture of an alkali lower alkoxide (e.g. sodium methoxide), a lower alkanol (e.g. methanol) and the 3-halo compound is autoclaved at about 200° C., the solvent is evaporated, the residue is treated with water, the aqueous mixture acidified, and the resultant solids collected to yield the 3-hydroxy compounds.

The 3-cyanopyridin-2(1H)-ones, (A), may be converted to the thiocarboxamide compounds VII as shown in reaction (3) below:

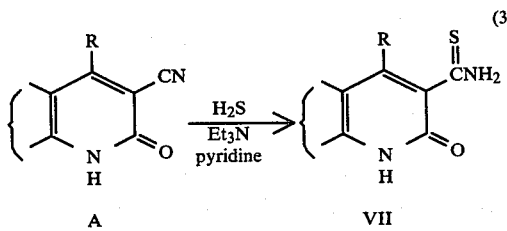

wherein R is as defined above.

This reaction (3) is known in the art and is described by J. Chem. Soc., 742–744 (1952). The conversion is accomplished by treating the 3-cyanopyridin2(1H)-one, (A), with hydrogen sulfide and triethylamine in pyridine at or above room temperature. The product, VII, is then isolated and purified by conventional procedures such as extraction, distillation, chromatography, filtration and the like.

The 3-cyanopyridin-2(1H)-ones (A), may also be converted to the carboxamidine Compound VIII by treatment with liquid ammonia and ammonium chloride at elevated temperatures (80° C.) as shown in reaction (4) below:

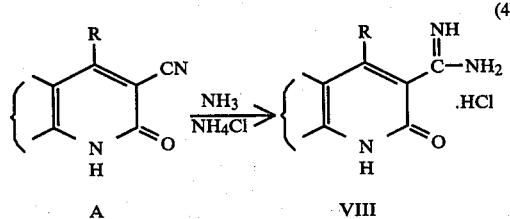

The following examples describe in detail the preparation of the compounds and compositions of the present invention. As used herein, the term "room temperature" refers to about 20° C. to 25° C. Unless otherwise stated, all temperature and temperature ranges are in degrees Celsius.

EXAMPLE 1

Preparation of 1-Dimethylaminomethylene-1,4-dihydro-3-benzopyran-2-one

Heat 8.8 gm of 1,4-dihydro-3-benzopyran-2-one and 12.0 ml of dimethylformamide dimethyl acetal under reflux for 1½ hours. Concentrate the reaction mixture in vacuo. Dissolve the residue in hot methanol, add charcoal, filter, and concentrate the filtrate in vacuo to give the title compound.

EXAMPLE 2

Preparation of 2-Cyano-4,6-dihydro-3H-[2]Benzopyrano[3,4-b]pyridin-3-one

Heat 5.7 gm of 1-dimethylaminomethylene-1,4-dihydro-3-benzopyran-2-one, 2.23 gm of cyanoacetamide and 3.3 gm of sodium methoxide in 100 ml of dimethylformamide for 8 hours at 80°. Cool and dilute the reaction mixture with 150 ml of acetonitrile. Isolate the title compound.

Similarly, the following compounds of this invention may be prepared by using the procedures of the above examples and employing the appropriate reagents:

3-cyano-[1]benzothieno[2,3-b]pyridin-2(1H)-one;
3-ethylthieno[2,3-b:5,4-b']dipyridin-2(1H)-one;
3-cyanothieno[2,3-b:5,4-b']dipyridin-2(1H)-one;
4-methylthieno[2,3-b:5,4-c']dipyridin-2(1H)-one;
3-cyanothieno[2,3-b:5,4-c']dipyridin-2(1H)-one;
3-cyano-4-methylthieno[2,3-b:5,4-c']dipyridin-2(1H)-one;
3-ethoxythieno[2,3-b:4,5-c']dipyridin-2(1H)-one;
3-cyanothieno[2,3-b:4,5-c']dipyridin-2(1H)-one;
3-cyano-4-ethylthieno[2,3-b:4,5-b']dipyridin-2(1H)-one;
3-cyanothieno[2,3-b:4,5-b']dipyridin-2(1H)-one;
3-cyanobenzofuro[2,3-b]pyridin-2(1H)-one;
3-cyanofuro[2,3-b:5,4-c']dipyridin-2(1H)-one;
3-cyanofuro[2,3-b:5,4-b']dipyridin-2(1H)-one;
3-cyano-4-methylfuro[2,3-b:5,4-c']dipyridin-2(1H)-one;
3-cyanofuro[2,3-b:4,5-c']dipyridin-2(1H)-one;
3-cyanofuro[2,3-b:4,5-b']dipyridin-2(1H)-one;
2-cyano-4,6-dihydro-3H-[2]benzopyrano[3,4-b]pyridin-3-one;
2-cyano-4,6-dihydro-1-n-propyl-3H-[2]benzopyrano[3,4-b]pyridin-3-one;
2,8-diethoxy-4,6-dihydro-3H-[2]benzopyrano[3,4-b]pyridin-3-one;
2-cyano-4,6-dihydro-1-methyl-3H-pyrano[2,3-b:5,4-b']dipyridin-3-one;
2-cyano-4,6-dihydro-3H-thiopyrano[2,3-b:5,4-b']dipyridin-3-one;
9-cyano-5,7-dihydro-3H-thiopyrano[2,3-b:5,4-b']dipyridin-8-one;
9-cyano-5,7-dihydro-8H-thiopyrano[2,3-b:4,5-c']dipyridin-8-one;
9-cyano-5,7-dihydro-8H-thiopyrano[2,3-b:4,5-b']dipyridin-8-one;
5,7-dihydro-2,3-dimethyl-9-ethoxy-8H-pyrano[2,3-b:4,5-b']dipyridin-8-one;
2-cyano-1-ethyl-5H-[1]benzothiopyrano[3,4-b]pyridin-3(4H)-one;
2-cyano-5H-[1]benzopyrano[3,4-b]pyridin-3(4H)-one;
2-methoxy-6H-thiopyrano[2,3-b:5,4-b']-dipyridin-3-(4H)-one;
9-cyano-6H-pyrano[3,2-b:5,4-b']dipyridin-8(7H)-one;
2-cyano-6,7-dihydro-[3]benzothiepino[2,1-b]pyridin-3(4H)-one;
9-cyano-5,8-dihydro-10-methylthiepino[2,3-b:4,5-b']dipyridin-9(6H)-one;
2-cyano-6,7-dihydro-[3]benzoxepino[2,1-b]pyridin-3(4H)-one;
2-cyano-6,7-dihydro-oxepino[2,3-b:5,4-b']dipyridin-3(4H)-one;
2-cyano-5,7-dihydro-[2]benzothiepino[4,5-b]pyridin-3(4H)-one;
10-cyano-5,7-dihydro-11-methylthiepino[3,4-b:6,5-c']dipyridin-9(8H)-one;
2-cyano-5,7-dihydro-[2]benzoepino[4,5-b]pyridin-3(4H)-one;
10-cyano-5,7-dihydro-11-methyloxepino[3,4-b:5,6-c']dipyridin-9(8H)-one;
2-cyano-5,6-dihydro-[1]benzothiepino[4,5-b]pyridin-3(4H)-one;
10-cyano-6,7-dihydro-11-methylthiepino[3,2-c:5,4-b']dipyridin-9(8H)-one;
2-cyano-5,6-dihydro[1]benzoxepino[4,5-b]pyridin-3(4H)-one; and
2-cyano-5,6-dihydro-1-ethyloxepino[2,3-b:5,4-b']dipyridin-3(4H)-one.

EXAMPLE 3

Preparation of 4,6-Dihydro-3H-[2]benzopyrano[3,4-b]pyridin-3-one-2-carboxamide Hydrochloride Heat 5.5 gm 2-cyano-4,6-dihydro-3H-[2]benzopyrano[3,4-b]pyridin-3-one in 50 ml of 90% sulfuric acid at 100° for 1½ hours. Cool the reaction mixture, pour into ice water and basify the aqueous mixture with 50% sodium hydroxide to give a precipitate. Filter the product and air-dry to give the title compound.

EXAMPLE 4

Preparation of 4,6-Dihydro-3H-[2]benzopyrano-3,4-b]-pyridin-3-one-2-carboxamide Hydrochloride Add 2.10 gm of 2-cyano-4,6-dihydro-3H[2]benzopyrano[3,4-b]-pyridin-3-one to 0.53 gm of ammonium chloride in liquid ammonia in a steel bomb. Heat the system to 80° C. for 24 hours. Cool the system to room temperature and remove the ammonia. Isolate the title compound.

EXAMPLE 5

Preparation of 4,6-Dihydro-3H[2]benzopyrano[3,4-b]pyridin-3-one-2-thiocarboxamide Add 4.20 gm of 2-cyano-4,6-dihydro-3H[2]benzopyrano[3,4-b]-pyridin-3-one to 50 gm of pyridine. Add 3.0 ml of triethylamine to the system. Cool the system to 0°-5° and treat the system with hydrogen sulfide gas until the reaction is complete as indicated by thin layer chromatography. Isolate the title compound.

EXAMPLE 6

Preparation of 4,6-Dihydro-3H[2]benzopyrano[3,4-b]pyridin-3-one-2-carboxylic acid Add 6.3 gm of 2-cyano-4,6-dihydro-3H[2]benzopyrano[3,4-b]pyridin-3-one to 100 ml of 50% aqueous sulfuric acid. Heat the system to reflux for 6 hours. Cool the reaction mixture, pour into ice water and isolate the title compound.

EXAMPLE 7

Preparation of Methyl 4,6-Dihydro-3H[2]benzopyrano[3,4-b]pyridin-3-one-2-carboxylate Add 6.0 gm of 4,6-dihydro-3H[2]benzopyrano[3,4-b]pyridin-3-one-2-carboxylic acid to 100 ml of methanol. Dropwise, at 0° C., add 10 ml of thionyl chloride to the system. Heat the system at reflux for 6 hours. Remove the solvent by stripping. Isolate the title compound.

EXAMPLE 8

Preparation of 4,6-Dihydro-3H-[2]benzopyrano[3,4-b]pyridin-3-one-2-N,N-dimethylcarboxamide Add 2.7 gm of methyl 4,6-dihydro-3H-[2]benzopyrano[3,4-b]pyridin-3-one-2-carboxylate to a steel bomb containing 40% aqueous methylamine. Heat the system in an oil bath at 100° for 16 hours. Stop the reaction and cool the system to room temperature. Extract the product with chloroform and wash the chloroform solution with water. Treat the chloroform solution with charcoal and then filter. Dry the chloroform solution with anhydrous sodium sulfate and filter. Remove the solvent by stripping to give the title compound.

Similarly, the following compounds of this invention may be prepared by using the above procedures and employing the appropriate starting materials:

[1]benzothieno[2,3-b]pyridin-2(1H)-one-3-carboxylic acid;

Methyl thieno[2,3-b-:5,4-c']dipyridin-2(1H)-one-3-carboxylate;

benzofuro[2,3-b]pyridin-2(1H)-one-3-carboxamide;

furo[2,3-b:5,4-b']dipyridin-2(1H)-one-3-thiocarboxamide;

4,6-dihydro-3H-[2]benzothiopyrano[3,4-b]pyridin-3-one-2-carboxamide;

5,7-dihydro-8H-thiopyrano[2,3-b:4,5-c']dipyridin-8-one-9-carboxylic acid;

5,7-dihydro-8H-pyrano[2,3-b:4,5-b']dipyridin-8-one-9-carboxylic acid;

4H-[1]benzothiopyrano[3,4-b]pyridin-3(5H)-one-2-thiocarboxamide;

6H-thiopyrano[2,3-c:5,4-b']dipyridin-8(7H)-one-9-carboxamidine;

1-methyl-4H-[1]benzopyrano[3,4-b]pyridin-3(4H)-2-thiocarboxamide;

6H-pyrano[2,3-b:5,4-b']dipyridin-8(7H)-one-9-carboxamidine;

6,7-dihydro-1-ethyl-[3]benzothiepino[2,1-b]pyridin-3(4H)-one-2-carboxylic acid;

6,7-dihydrothiepino[2,3-b:5,4-b']dipyridin-3(4H)-one-2-carboxamide;

Methyl 6,7-dihydro-[3]benzoxepino[2,1-b]-pyridin-3(4H)-one-2-carboxylate;

5,8-dihydro-oxepino[2,3-b:4,5-c']dipyridin-9(6H)-one-10-thiocarboxamide;

5,7-dihydro-[2]benzothiepino[4,5-b]pyridin-3(4H)-one-2-carboxamidine;

5,7-dihydrothiepino[3,4-b:5,6-b']dipyridin-9(8H)-one-10-carboxamide;

5,7-dihydro-[2]benzoxepino[4,5-b]pyridin-3(4H)-one-2-carboxylic acid;

6,7-dihydrothiepino[2,3-c:5,4-b']dipyridin-9(8H)-one-2-thiocarboxamide; and 5,6-dihydro-oxepino[2,3-b:5,4-b']dipyridin-3(4H)-one-2-carboxamidine.

EXAMPLE 9

Preparation of 2-Amino-4,6-dihydro-3H[2]benzopyrano[3,4-b]pryridin-3-one

Add 3.65 gm of 4,6-dihydro-3H[2]benzopyrano[3,4-b]pyridin-3-one-2-carboxamide to a solution of 4.2 gm of sodium hydroxide in 65 ml of water containing 1.05 ml of bromine at 0°-5° C. Stir the resulting mixture at 100° for 3 hours. Cool and acidify the reaction mixture with concentrated hydrochloric acid. Stir this solution for 45 minutes and then cool this solution to give a precipitate. Filter the mixture to give the title compound.

EXAMPLE 10

Preparation of 2-(N-acetylamino)-4,6-dihydro-3H[2]benzopyrano[3,4-b]pyridin-3-one To 2.0 gm of 2-amino-4,6-dihydro-3H-[2]benzopyrano[3,4-b]pyridin-3-one, in 100 ml of chloroform containing 1 ml of pyridine, add 0.80 gm of acetyl chloride. Stir the reaction at room temperature for 5 hours. Filter and wash the solution with water. Remove the solvent by stripping to give the title compound.

Similarly, the following compounds of this invention may be prepared by using the above procedures and employing the appropriate starting materials:

3-amino-[1]benzothieno[2,3-b]pyridin-2(1H)-one;
3-amino-5-methylfuro[2,3-b:5,4-c']dipyridin-2(1H)-one;
2-amino-9-chloro-4,6-dihydro-3H-thiopyrano-[2,3-b:5,4-b']dipyridin-3-one;
9-(N-acetylamino)-5,7-dihydro-8H-pyrano-[2,3-b:4,5-c']dipyridin-8-one;
9-(N-acetylamino)-6H-thiopyrano[3,2-b:5,4-b']dipyridin-8(7H)-one;
9-amino-6H-pyrano[2,3-c:5,4-b']dipyridin-8(7H)-one;
10-amino-5,8-dihydrothiepino[2,3-b:4,5-c']dipyridin-9(6H)-one;
10-amino-5,7-dihydroxepino[3,4-b:5,6-c']dipyridin-9(8H)-one;
10-amino-6,7-dihydro-1,4-dimethylthiepino[3,2-c:5,4-b']dipyridin-9(8H)-one; and
10-amino-5,6-dihydro-4-methoxyoxepino[3,2-b:5,4-b']dipyridin-9(8H)-one.

EXAMPLE 11

Preparation of 2-chloro-4,6-dihydro-3H[2]benzopyrano[3,4-b]pyridin-3-one (a) To a mixture of 60 ml of concentrated sulfuric acid and 15 ml of water, add 22.2 gm of 4,6-dihydro-3H[2]benzopyrano-[3,4-b]pyridin-3-one-2-carboxylic acid. Heat the system at reflux for 24 hours. Cool the system and pour the solution into 1 liter of ice/water. Neutralize the solution with 10N NaOH solution. Extract the solution with 300 ml of chloroform and dry the organic solution over anhydrous magnesium sulfate. Filter the solution and remove the solvent by stripping to give 4,6-dihydro-3H[2]-benzopyrano-[3,4-b]pyridin-3-one.

(b) Add 19.7 gm of 4,6-dihydro-3H[2]benzopyrano-[3,4-b]pyridin-3-one to 300 ml of acetic acid. Bubble chlorine into the reaction solution for 4 hours at 100°. Cool the system and collect the product as a precipitate. Dissolve the solid into water and neutralize the solution with 1N NaOH. Extract the product with chloroform. Dry the chloroform over anhydrous magnesium sulfate and filter the solution. Remove the solvent by stripping to give the title compound.

EXAMPLE 12

Preparation of 2-(N-methylamino)-4,6-dihydro-3H[2]-benzopyrano[3,4-b]pyridin-3-one Add 23.1 gm of 2-chloro-4,6-dihydro-3H[2]benzopyrano[3,4-b]pyridin-3-one to 100 ml of 40% aqueous methylamine and 250 ml of water. Heat the system in a steel bomb at 140° C. for 5 days. Stop the reaction and isolate the title compound.

EXAMPLE 13

Preparation of 2-hydroxy-4,6-dihydro-3H[2]benzopyrano[3,4-b]pyridin-3-one

Add 23.1 gm of 2-chloro-4,6-dihydro-3H[2]benzopyrano[3,4-b]pyridin-3-one to 300 ml of methanol containing 30 gm of sodium methoxide. Heat the system in a steel bomb at about 200° C. for 12 hours. Stop the reaction and remove the solvent by stripping. Treat the residue with water and then isolate the title compound.

EXAMPLE 14

Preparation of 2-cyano-4,6-dihydro-3H[2]benzothiopyrano[3,4-b]pyridin-3-one-5,5-dioxide Add 22.6 gm of 2-cyano-4,6-dihydro-3H[2]benzothiopyrano[3,4-b]pyridin-3-one to 150 ml of chloroform. Add 30.0 gm of m-chloroperbenzoic acid to the system. Stir the system at room temperature for 18 hours. Wash the organic solution first with saturated sodium bisulfite solution (2×500 ml) and then with saturated sodium bicarbonate solution (2×500 ml). Dry the organic solution over anhydrous magnesium sulfate, filter, and remove the chloroform by stripping to give the title compound.

The following formulations exemplify some of the dosage forms in which the compounds of this invention may be employed. In each, the active ingredient is designated by the term "Drug" which is meant to indicate the following compound:

2-cyano-4,6-dihydro-3H-[2]benzopyrano[3,4-b]pyridine-3-one

It is contemplated, however, that each of these exemplar compounds may be replaced by equally effective quantities of other compounds within the scope of formula I. All temperatures are in degrees Celsius.

EXAMPLE 15

Parenteral Dosage Forms (a) Injection (Per vial)

|  | mg/vial |
| --- | --- |
| Drug Sterile Powder | 500 |

Add sterile water for injection or bacteriostatic water for injection for reconstitution.

(b) Injectable Solution of drug

| Ingredient | mg/ml |
| --- | --- |
| Drug | 20 |
| Methylparaben | 0.2 |
| Propylparaben | 1.6 |
| Sodium Bisulfite | 3.2 |
| Disodium Edetate | 0.1 |
| Water for Injection, q.s. ad | 1.0 ml |

METHOD OF MANUFACTURE

1. Dissolve parabens in portion (85% of the final volume) of the water for injection at 65°–70°.
2. Cool to 25°–35°. Charge and dissolve the sodium bisulfite and disodium edetate.
3. Charge and dissolve Drug.
4. Bring the solution to final volume by adding water for injection.
5. Filter the solution through 0.22 membrane and fill into appropriate containers.
6. Terminally sterilize the units by autoclaving.

We claim:
1. A compound of the formula

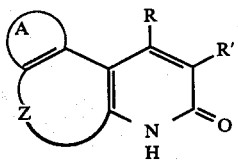

wherein

R is hydrogen or lower alkyl;

R¹ is hydrogen, hydroxy, lower alkoxy, cyano, lower alkyl, halogen, —NR²R³, —CONR²R³, —NHCOR², —COOR² (wherein R² and R³ are independently hydrogen, lower alkyl, or hydroxy lower alkyl) or

—CNH₂ wherein M is sulfur or NH; with the proviso that R and R¹ are not both hydrogen;

Z is selected from the group consisting of

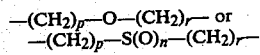

wherein n is 0, 1, or 2; and p and r are independently 0, 1, 2 or 3 with the further proviso that r and p is three or less;

A is a substituted or unsubstituted benzo ring which when substituted have 1 to 3 substituents independently selected from halogen, hydroxy, lower alkyl and lower alkoxy;

or a pharmaceutically acceptable salt thereof.

2. A compound of claim 1 wherein R¹ is hydroxy, lower alkoxy, cyano, —NR²R³, —CONR²R³, —NR-COR² wherein R² and R³ are independently hydrogen, lower alkyl or hydroxy lower alkyl.

3. A compound of claim 2 wherein R¹ is cyano, amino or

—CNH₂.

4. A compound of claim 1 wherein R is hydrogen or methyl.

5. A compound of claim 1 wherein Z is —(CH₂-)$_p$—O—(CH₂)$_r$— wherein R, R¹, p, r and A are as defined in claim 1.

6. A compound of claim 5 wherein p is zero and r is 1.

7. A compound of claim 6 wherein R is hydrogen and R¹ is cyano.

8. A compound of claim 7 wherein A is a benzo group; i.e., 2-cyano-4,6-dihydro-3H-[2]benzopyrano[3,4-b]pyridin-3-one.

9. A method for increasing cardiac contractility in a human patient requiring such treatment which comprises parenterally administering an amount of a compound defined in claim 1 effective in increasing cardiac contractility.

10. A method of increasing cardiac contractility in a human patient requiring such treatment which comprises parenterally administering an amount of the compound defined in claim 8 effective in increasing cardiac contractility.

11. A pharmaceutical composition comprising a pharmaceutically acceptable carrier and an amount of a compound defined in claim 1 effective in increasing cardiac contractility in humans in need of such treatment.

12. A pharmaceutical composition comprising a pharmaceutically acceptable carrier and an amount of the compound defined in claim 8 effective in increasing cardiac contractility in humans in need of such treatment.

* * * * *